United States Patent

Su et al.

[11] Patent Number: 6,124,492
[45] Date of Patent: Sep. 26, 2000

[54] PROCESS FOR PREPARING BIS(3-T-BUTYL-4-HYDROXYPHENYL-2,4-DI-T-BUTYLPHENYL)RESORCINOL DIPHOSPHATE

[75] Inventors: Wen Chiung Su; Yie Shun Chiu, both of Taipei, Taiwan

[73] Assignee: Chung Shan Institute of Science and Technology, Tao Yuan, Taiwan

[21] Appl. No.: 09/264,681

[22] Filed: Mar. 9, 1999

[51] Int. Cl.[7] ...................................................... C07F 9/12
[52] U.S. Cl. .......................................... 558/100; 558/162
[58] Field of Search ..................................... 558/100, 162

[56] References Cited

U.S. PATENT DOCUMENTS 2,520,090   8/1950   Barrett ..................................... 558/162
5,756,798   5/1998   Stults .................................. 558/162 X

*Primary Examiner*—Michael G. Ambrose
*Attorney, Agent, or Firm*—Rosenberg, Klein & Lee

[57] ABSTRACT

The invention relates to a process for preparing bis(3-t-butyl-4-hydroxyphenyl-2,4-di-t-butylphenyl)resorcinol diphosphate, which has characteristics of high conversion and high selectivity, and which comprises of charging sequentially phenolic compounds, phosphoryl chloride, catalyst and organic base, heating the reaction mixture for carry out a three-stage esterification reaction and improving the purity of the product through molecular designing; dissolving the product in an organic solvent and removing residual hydrochloride salt with a small amount of ammonia gas, thereby achieving the object of purification without generation of waste water and waste product.

11 Claims, No Drawings

PROCESS FOR PREPARING BIS(3-T-BUTYL-4-HYDROXYPHENYL-2,4-DI-T-BUTYLPHENYL)RESORCINOL DIPHOSPHATE

BACKGROUND OF THE INVENTION

1. Field of the Invention

The invention relates to a process for preparing bis(3-t-butyl-4-hydroxyphenyl-2,4-di-t-butylphenyl)resorcinol diphosphate.

2. Description of Related Art

Bis(3-t-butyl-4-hydroxyphenyl-2,4-di-t-butylphenyl) resorcinol diphosphate(HDP) is considered as a homologous compound in the production process thereof, which has a following structure:

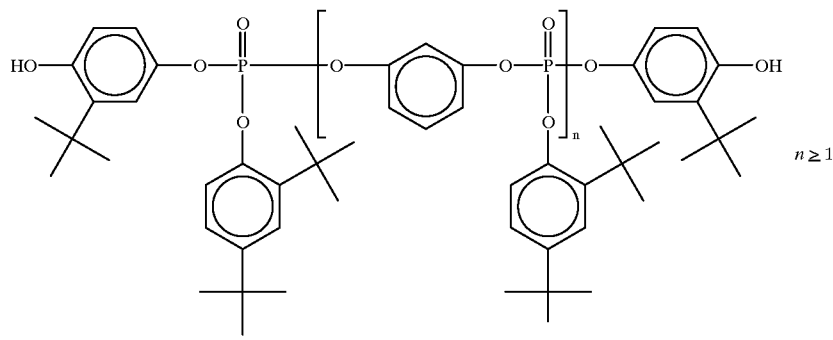

HDP is a flame retardant of aromatic phosphorous series and is suitable for bonding with monomers such as, for example, monomers of epoxy resin. The product obtained after polymerizing can retain their physical and chemical properties as well as their weathering resistance that makes them being an environment friendly product in the future.

Processes for synthesizing hydroxy-reactive flame retardant of aromatic phosphorous series, such as those described in U.S. Pat. No. 5,506,313 (1996) and U.S. Pat. No. 5,278,212 (1994), provided a product as a mixture having a low proportion of the main component, and did not disclose the manner of purification or washing of products with aqueous solution of hydrochloric acid. The main disclosure thereof comprised of demonstrating the slowing of the physical and chemical changes after reaction of the hydroxy aromatic phosphorous-based flame retardant Objects of the present invention are, therefore, intended to increase the purity of a single product, to improve the reproducibility of the reaction and to simplify the reaction steps so as to provide the feasibility of mass production The above-described objects can be accomplished by a process for preparing bis(3-t-butyl-4-hydroxyphenyl-2,4-di-t-butylphenyl)-resorcinol diphosphate according to the invention.

SUMMARY OF THE INVENTION

The process for preparing bis(3-t-butyl-4-hydroxyphenyl-2,4-di-t-butylphenyl) resorcinol diphosphate according to the invention comprises as the first stage of charging phosphoryl chloride, resorcinol and magnesium chloride once in a reactor, heating and reacting the reaction mixture at a temperature of 80~100° C. for 3 hours, and evaporating the excess phosphoryl chloride; then as the second stage of charging 2,4-di-t-butylphenol and organic base and reacting at 120~130° C. for 2 hours; and as the third stage of charging t-butylhydroquinone and reacting at 120~130° C. for 2 hours. These three stages of reaction are analyzed by $^{31}P$ nuclear resonance spectroscopy for completing of reactions. Thereafter, the product is dissolved in an organic solvent. The hydrochloride salt of the organic base therein is filtered off. The small amount of the residual hydrochloride salt in the filtrate is converted into ammonium chloride with ammonia. A HDP homologous compound can be obtained after filtering off the ammonium chloride following by evaporating and recycling the organic solvent. Its conversion, calculated based on resorcinol, can be up to 100% of theoretical value and its selectivity is higher than 80%.

DETAILED DESCRIPTION OF THE PREFERRED EMBODIMENT

According to the invention, the preparation of bis(3-t-butyl-4-hydroxyphenyl-2,4-di-t-butylphenyl) resorcinol diphosphate (HDP) is carried out in a 3-stage one-pot process. In the first stage, resorcinol, excess phosphoryl chloride and trace of magnesium chloride as catalyst are charged in a reactor equipped with a temperature probe and a condenser which is provided with a gas inlet for introducing hydrogen chloride gas into a neutralizing tank.

In the first stage, a esterification reaction is carried out at a temperature of 60~120° C. and under normal pressure. Its main product is a mono-substituted product (n=1) with minor di-substituted products (n=2) as shown in the following equation (1).

The reaction temperature is preferable controlled at 80~100° C., otherwise, the great amount of hydrogen chloride gas produced by reacting at higher temperature will entrain phosphoryl chloride out of the reactor. Then, after about 3 hours, a distillation under reduced pressure (30~40 mmHg) can be performed for recovery of excess phosphoryl chloride, wherein, the temperature should not exceed desirably over 130° C. in order to avoid the reverse reaction.

When no more phosphoryl chloride can be distilled off after about 3 hours and the reaction is brought to room temperature, one equivalent of 2,4-di-t-butylphenol and two equivalent of an organic base are added for carrying out the second esterification reaction as shown in the following equation (2) at a temperature controlled at 80~140° C., preferably at 120~130° C., for 2 hours.

Thereafter, one equivalent of t-butylhydroquinone is added to carry out the third esterification reaction as shown in the following equation (3) at a temperature controlled at 70~140° C., preferably at 120~130° C. for 2 hours. After each of those three esterification reactions, $^{31}$P nuclear resonance spectroscopy is performed to detect the end point of the reaction, respectively. When reactions are completed, the product is dissolved in an organic solvent, the reaction mixture is brought to room temperature, and the hydrochloride salt of organic base therein is filtered off. Then, the residual hydrochloride salt in the filtrate is converted into ammonium chloride with a small amount of ammonia gas. The HDP product can be obtained by filtering off the ammonium chloride and recovering the organic solvent. The overall conversion calculated based on resorcinol is up to 100% of theoretical value and the selectivity is higher than 80%.

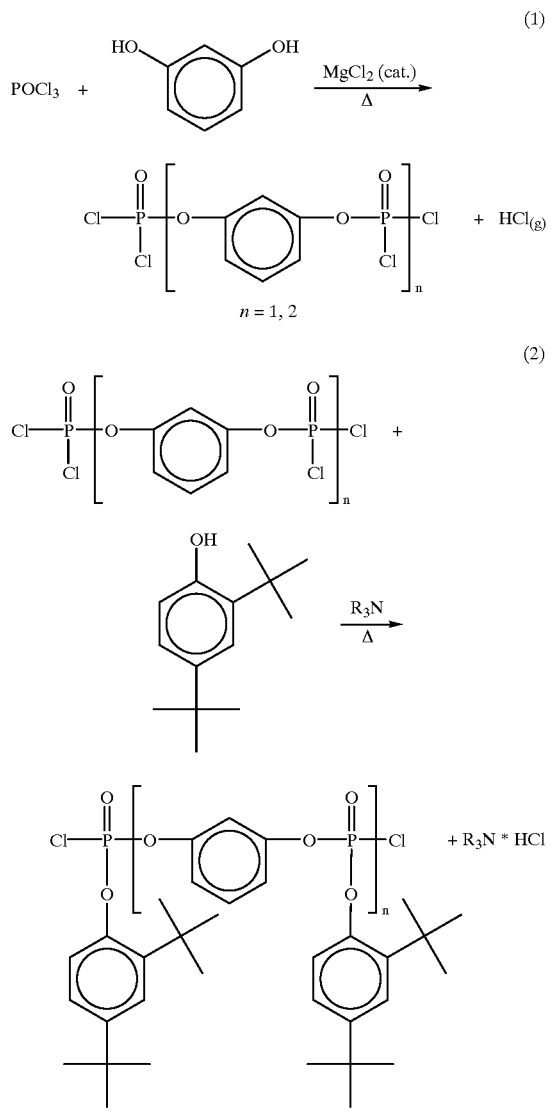

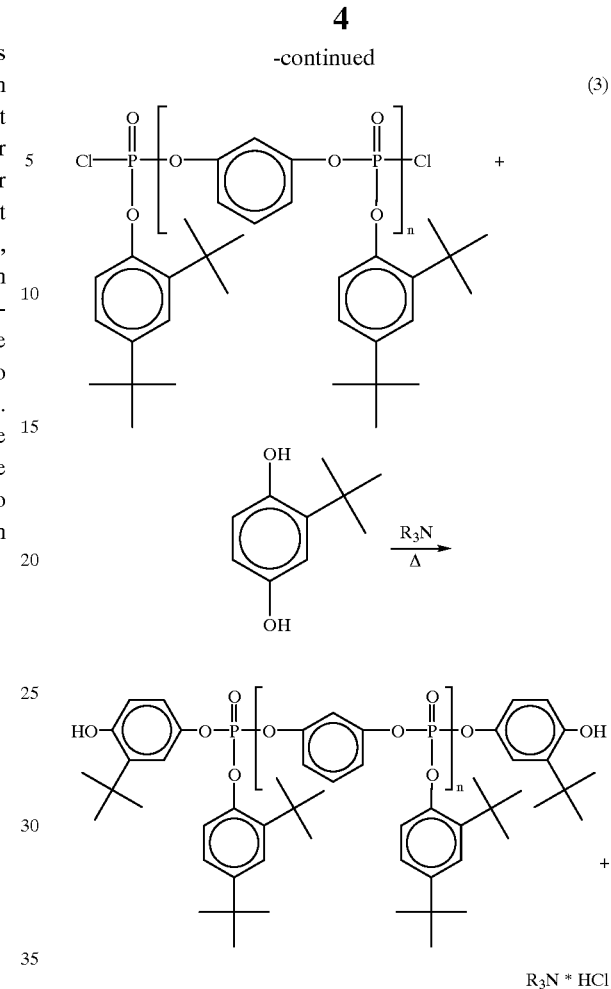

In various embodiments of the present invention, the mono-substituted product of the first stage esterification reaction includes a tetrachloro resorcinol diphosphate, as shown in the structural formulations of the chemical equations shown above. Also in various embodiments, the phosphoryl chloride used preferably ranges between 4 to 8 times by mole relative to the amount of resorcinol used, and the amount of magnesium chloride used ranges approximately between 0.1% to 1% by weight relative to the phosphoryl chloride. Preferably, the amount of magnesium chloride used is 0.4% by weight relative to the phosphoryl chloride. Moreover, pyridine or triethylamine may be used as an organic base in an esterification reaction stage. The organic solvent used following the third stage esterification reaction preferably includes toluene, xylene, ethyl acetate, or butyl acetate, and the amount of the organic solvent used is approximately 5 times by weight relative to the final product.

The invention will be illustrated further in the following examples.

EXAMPLE 1

11 g (0.1 mole) resorcinol, 92 g (0.6 mole) phosphoryl chloride and 0.36 g (0.4% by weight of the phosphoryl chloride) magnesium chloride as catalyst were weighed and added simultaneously in a 250-ml reactor which was provided with a temperature probe and a condenser. The cooling medium in the condenser was kept at 0° C. and there was a gas inlet tube provided on the condenser for inducing hydrogen chloride gas into a neutralizing tank. The reaction solution was brought to a temperature of about 65° C. to start the reaction.

After reacting by keeping temperature at 80~100° C. for about one hour, the generating rate of hydrogen chloride gas was slowed down. The reaction was almost completed after three hours. At this time, a sample was taken from the reaction mixture and an external standard, tris(2-chloroethyl) phosphate (TCEP), was added. By performing $^{31}$P nuclear resonance spectroscopy thereon, the relative integration area of peaks observed can be converted into the conversion of the reaction. After recovering the excess phosphoryl chloride by evaporating under reduced pressure, a product of 33.36 g was obtained, which demonstrated duplicately a conversion of 100% by comparison with the theoretical value of 33.33 g.

A second stage of esterification reaction was followed. Based on the relative integration value, 37.66 g (0.183 mole) 2,4-di-t-butylphenol and 33.3 g (0.42 mole) pyridine were added into the above-obtained intermediate product. The condenser was cooled by circulating water and the reaction temperature was maintained at 120~130° C. for 2 hours. Then, a sample was taken from the reaction mixture and was detected by $^{31}$P nuclear resonance spectroscopy to show the completeness of the reaction wherein products having selectivity of higher than 90% were di-substituted products, as shown in Table 1.

Finally, the third stage esterification reaction was carried out by adding 31.66 g (0.19 mole) t-butylhydroquinone and keeping the reaction temperature at 120~130° C. for 2 hours. A sample was taken and detected by $^{31}$P nuclear resonance spectroscopy to show that the reaction was completed and a tri-substituted HDP product was obtained. The product was dissolved in 150 g toluene. The pyridium hydrochloride was filtered off at room temperature and the filtrate was distilled to recover toluene. A preliminarily purified HDP was thus obtained, which had test values as shown in Table 2.

$^{31}$P NMR spectrum (ppm reference point is 85% $H_3PO_4$)

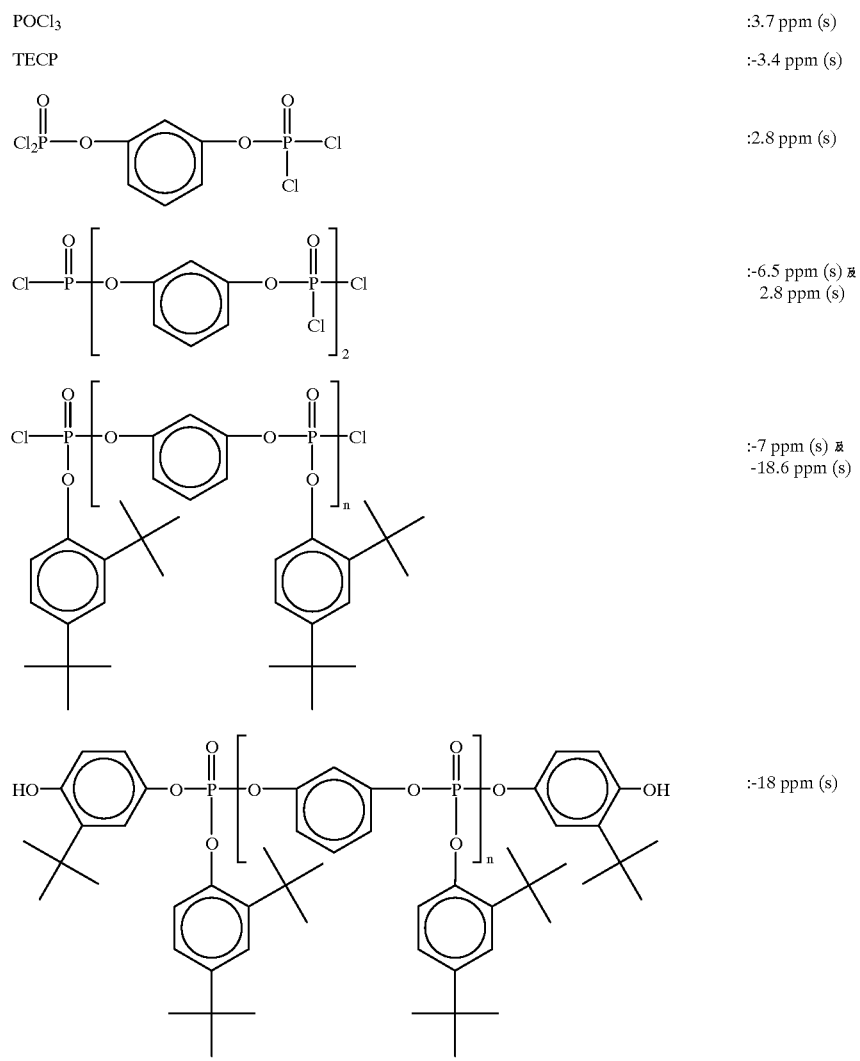

-continued

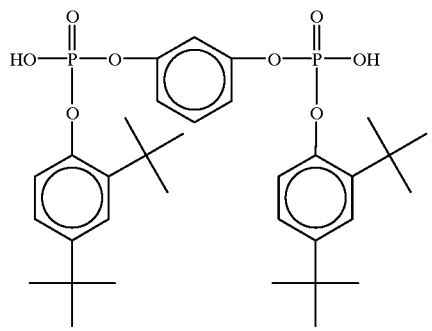

:-12 ppm (s)

EXAMPLE 2–4

Reaction conditions in the first and third stage esterification were in the same manner as in Example 1, only temperature and time period used in the second stage esterification were changed as shown in Table 1.

EXAMPLE 5–12

The first stage esterification reaction was carried out under the same conditions as in Example 1. The second stage esterification was performed by dissolving reactants in 150 ml organic solvent containing 37.66 g (0.183 mole) 2,4-di-t-butylphenol at room temperature, dropping 22.18 g (0.22 mole) triethylamine in the reaction solution at 25° C. or 0° C. After reacting for 16 hours or one hour, the reaction was detected by $^{31}P$ nuclear resonance spectroscopy. The conversion rate and selectivity thereof were calculated based on relative integration values. Results thereof were shown in Table 1.

The third stage esterification was followed by adding 31.66 g (0.19 mole) t-butylhydroquinone in the solution and dropping 19.19 g (0.19 mole) triethylamine at 25° C. After reacting for 16 hours, the triethylammonium chloride was filtered off and the filtrate was detected by $^{31}P$ nuclear resonance spectroscopy. It was shown that the reaction was converted completely into HDP and its derivatives (75~90%) as well as bis(2,4-di-t-butylphenyl)resorcinol diphosphate (10~25%).

EXAMPLE 13

The conditions of all those three stage esterification reactions were the same as in the Example 1, except that, during purification, the product was dissolved in toluene and the pyridium hydrochloride therein was filtered off. A small amount of ammonia gas was bubbled thereinto for about 5 minutes and stopped as the solution turned into light red, the ammonium chloride was filtered off and toluene was recovered. Test values of the product thereof were shown in Table 2.

EXAMPLE 14

Conditions for all those three stage esterification reactions and for the purification were the same as in Example 1, except that the organic solvent used was ethyl acetate. Test values of the product thereof were shown in Table 2.

EXAMPLE 15

Conditions for all those three stage esterification reactions and for the purification were the same as in Example 13, except that the 5 organic solvent used was ethyl acetate. Test values of the product thereof were shown in Table 2.

TABLE 1

Conditions for the second esterification reaction and results thereof.

| | Base (solvent) | Reaction Temp. (° C.) | Reaction time (hr) | Conversion (%) | Selectivity (%) |
|---|---|---|---|---|---|
| Ex. 1 | Pyridine (none) | 120 | 2 | 100 | 94 |
| Ex. 2 | Pyridine (none) | 100 | 4 | 99 | 85 |
| Ex. 3 | Pyridine (none) | 70 | 8 | 100 | 89 |
| Ex. 4 | Pyridine (none) | 25 | 18 | 95 | 91 |
| Ex. 5 | Et$_3$N (EtOAc) | 25 | 16 | 100 | 88 |
| Ex. 6 | Et$_3$N (acetone) | 25 | 16 | 91 | 90 |
| Ex. 7 | Et$_3$N (ether) | 25 | 16 | 95 | 77 |
| Ex. 8 | Et$_3$N (CH$_2$Cl$_2$) | 25 | 16 | 95 | 78 |
| Ex. 9 | Et$_3$N (EtOAc) | 0 | 1 | 89 | 80 |
| Ex. 10 | Et$_3$N (acetone) | 0 | 1 | 90 | 60 |
| Ex. 11 | Et$_3$N (ether) | 0 | 1 | 93 | 83 |
| Ex. 12 | Et$_3$N (CH$_2$Cl$_2$) | 0 | 1 | 94 | 75 |

Note:
Selectivity was referred to the ratio between products in the reaction equation (2).

TABLE 2

Test values of products.

| | Color | P content (%) | Cl content (ppm) | OH value (meq/g) |
|---|---|---|---|---|
| Ex. 1 | Pale yellow | 6.46 | 1220 | 1.48 |
| Ex. 13 | Pale yellow | 6.43 | 245 | 1.53 |
| Ex. 14 | Pale yellow | 6.48 | 8000 | 1.61 |
| Ex. 15 | Pale yellow | 6.38 | 30 | 1.56 |

Many changes and modifications in the above-described embodiments of the invention can, of course, be carried out without departing from the scope thereof. Accordingly, to promote the progress in science and the useful arts, the invention is disclosed and is intended to be limited only by the scope of the appended claims.

What is claimed is:

1. A process for preparing bis(3-t-butyl-4-hydroxyphenyl-2,4-di-t-butylphenyl)_resorcinol diphosphate (HDP), comprising the steps of:

(1) heating resorcinol, excess phosphoryl chloride and a predetermined amount of magnesium chloride as catalyst for carrying out a first stage esterification reaction to yield a mono-substituted product as a main intermediate;

(2) distilling and recovering un-reacted phosphoryl chloride, adding a predetermined amount of 2,4-di-t-butylphenol and an organic base, and heating for carrying out a second stage esterification reaction;

(3) at the end of the second stage esterification reaction, adding further a predetermined amount of t-butylhydroquinone and heating for carrying out a third stage esterification reaction;

(4) after substantial completion of the reaction, adding organic solvent, filtering off the hydrochloride salt of organic base, converting residual hydrochloride salt into ammonium chloride with a predetermined amount of ammonia gas, filtering off said ammonium chloride, and evaporating off said organic solvent from the filtrate under reduced pressure to thereby obtain HDP.

2. A process as in claim 1, wherein said predetermined amount of said phosphoryl chloride is approximately 4 to 8 times by mole of the amount of resorcinol.

3. A process as in claim 1, wherein said predetermined amount of magnesium chloride is approximately 0.1 to 1% by weight relative to phosphoryl chloride.

4. A process as in claim 3, wherein said predetermined amount of magnesium chloride is preferably 0.4% by weight relative to phosphoryl chloride.

5. A process as in claim 1, wherein the heating temperature for said first stage esterification reaction is 60~120° C.

6. A process as in claim 1, wherein the heating temperature for said second and third stage esterification reactions is 70~140° C.

7. A process as in claim 1, wherein the completion of said esterification reactions of steps (1), (2), and (3) is determined by identifying the reaction product by $^{31}$P nuclear resonance spectroscopy.

8. A process as in claim 1, wherein said organic base in said step (2) is pyridine.

9. A process as in claim 1, wherein said organic solvent in said step (4) is selected from the group consisting of toluene, xylene, ethyl acetate, or butyl acetate.

10. A process as in claim 9, wherein the amount of said organic solvent used is 5 times the weight of the HDP.

11. A process as in claim 8, wherein said mono-substituted product includes tetrachloro resorcinol diphosphate.

* * * * *